United States Patent [19]

Bruner, Jr.

[11] Patent Number: 4,692,549
[45] Date of Patent: Sep. 8, 1987

[54] CARBOALKOXYLATION OF BUTADIENE TO FORM DIALKYL ADIPATE

[75] Inventor: Harold S. Bruner, Jr., Hockessin, Del.

[73] Assignee: E. I. Du Pont de Nemours and Company, Wilmington, Del.

[21] Appl. No.: 879,399

[22] Filed: Jun. 27, 1986

[51] Int. Cl.$^4$ ............................................. C07C 67/38
[52] U.S. Cl. ..................................... 560/204; 560/190; 562/590
[58] Field of Search ................. 560/204, 190; 562/590

[56] References Cited

U.S. PATENT DOCUMENTS

| | | | |
|---|---|---|---|
| 4,169,956 | 10/1979 | Kummer et al. | 560/204 |
| 4,404,394 | 9/1983 | Isogai et al. | 560/204 |
| 4,485,255 | 11/1984 | Jenck | 560/193 |
| 4,508,917 | 4/1985 | Jenck | 560/204 |
| 4,570,016 | 2/1986 | Bruner et al. | 560/204 |

Primary Examiner—Werren B. Lone
Assistant Examiner—Vera C. Clarke

[57] ABSTRACT

Production of dialkyl adipate by reaction of butadiene, carbon dioxide, and a lower alkyl alcohol in the presence of a cobalt catalyst and a tertiary nitrogen base cocatalyst to form a liquid mixture containing alkyl 3-pentenoate, adding alkanoic acid to the mixture in an amount sufficient to keep the cobalt catalyst active, and then reacting the mixture to form dialkyl adipate. The acid addition increases the rate of reaction relative to catalyst deactivation rate and reduces the consumption of the tertiary nitrogen base cocatalyst.

11 Claims, No Drawings

CARBOALKOXYLATION OF BUTADIENE TO FORM DIALKYL ADIPATE

BACKGROUND OF THE INVENTION

This invention relates to the preparation of dialkyl adipate, by the carboalkoxylation of butadiene.

The preparation of dialkyl adipate by the reaction of carbon monoxide and a lower alkyl alcohol with butadiene in the presence of cobalt catalysts and teritiary nitrogen base cocatalysts, i.e., pyridine, is known —see, for example, Kummer, et al U.S. Pat. No. 4,169,956, and Bruner, et al U.S. Pat. No. 4,570,016. The Kummer, et al process produces the diester by two reactions; first, producing the mono ester, i.e., alkyl 3-pentenoate, then separating a portion of the pyridine, and then reacting the alkyl 3-pentenoate to form the dialkyl adipate. The Bruner, et al process also employs two reactions, and between the reactions, the cobalt catalyst is regenerated by contact with a strongly acidic ion exchange resin.

Kummer, et al U.S. Pat. No. 4,169,956 discloses at Column 5 line 27 the addition of hydrogen to the reaction mixture of pentenoic acid ester, carbon monoxide and alcohol to increase the rate of reaction.

German Pat. No. 1,618,156 to BASF discloses the reaction of ethyl 3-pentenoate with carbon monoxide and an alcohol to form acid esters using a cobalt catalyst, pyridine cocatalyst, in the presence of water —see Example 8—to form diethyl adipate.

SUMMARY OF THE INVENTION

The present invention is based on the discovery that the amount of pyridine cocatalyst destroyed during the formation of dialkyl adipate from a mixture containing alkyl 3-pentenoate, cobalt catalyst, pyridine cocatalyst, a lower alkyl alcohol and carbon monoxide, can be greatly reduced by the addition of an amount of an alkanoic acid having a pKa greater than 3, in an amount sufficient to keep the cobalt catalyst active during the carboalkoxylation of the alkyl 3-pentenoate By use of the present invention, dialkyl adipate can be produced at high yields by the carboalkoxylation of butadiene with carbon monoxide and a lower alkyl alcohol, i.e., $C_1$ to $C_4$, without the necessity of pyridine separation or intermediate catalyst regeneration, by employing in both steps of the reaction a particular concentration range of cobalt catalyst, a particular concentration range of tertiary nitrogen base cocatalyst, and by the addition of a particular range of alkanoic acid to the product mixture of the first reaction stage, i.e., the mixture containing alkyl 3-pentenoate, prior to the second reaction to produce dialkyl adipate. Optionally, it is often desirable to also add a sufficient amount of inert diluent to reduce the concentration of the components in the first reaction by 5 to 15% before proceeding to the second reaction.

DETAILED DESCRIPTION OF THE INVENTION

The cobalt catalyst should be present in the butadiene containing reaction mixture at the beginning of the first reaction at a concentration of at least 0.5 moles per liter of liquid reaction mixture, and the tertiary nitrogen base cocatalyst should be present, in this reaction liquid mixture at a concentration in the range of between about 2.3 and 2.9 moles per liter of liquid reaction mixture. At the beginning of the first step of the reaction, the liquid mixture should contain between 38 and 50 parts by weight butadiene, 27 to 180 parts by weight alkyl alcohol, 180 to 230 parts by weight tertiary nitrogen base cocatalyst, and at least 29 parts by weight cobalt.

When a substantial amount of alkyl 3-pentenoate has been formed, or when the reaction is nearly complete, an alkanoic acid having a pKa greater than 3, preferably between about 4 and about 5, is added to the mixture containing among other things alkyl 3-pentenoate, cobalt catalyst, and tertiary nitrogen base cocatalyst. The amount of alkanoic acid added should be sufficient to keep the cobalt catalyst active, but less than about one mole per liter of the liquid formed in the first reaction, usually about 0.05 mole to 0.5 mole. The alkanoic acids that are preferred are adipic, methylglutaric, ethylsuccinic, propylmalonic, valeric, methylbutyric, and any isomer of pentenoic acid. Acetic acid is also satisfactory.

Also after formation of alkyl 3-pentenoate, optionally an inert diluent may be added to reduce the concentration of the components in the product of the first reaction by 5 to 15% before proceeding to the second reaction This addition permits regulation of the concentration of catalyst and cocatalyst for each reaction step. Larger dilutions will unnecessarily enlarge process volume. Suitable diluents for this purpose are methyl esters that are also produced during the reactions, or hydrocarbons.

The addition of acid increases the rate of the reaction, i.e., the formation of dialkyl adipate from alkyl 3-pentenoate, without raising the yield of undesirable by-products, e.g., methyl valerate. The acid addition also increases the rate of reaction relative to the catalyst deactivation rate, thereby reducing the consumption of pyridine.

The addition of acid affects the natural equilibrium that exists between the tertiary nitrogen base cocatalyst, e.g., pyridine, and the cobalt catalyst, e.g., $HCo(CO)_4$, and increases the amount of active catalyst. This is illustrated by the following equation

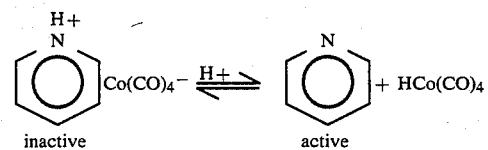

In addition to pyridine, other suitable tertiary nitrogen base cocatalysts are methyl pyridines, e.g., 3-picoline and isoquinoline, as well as trialkylamines, e.g., trimethylamine or triethylamine.

The cobalt catalyst employed in this invention is either cobalt carbonyl or a cobalt hydrocarbonyl. Typically, the cobalt catalyst is prepared by dissolving a cobalt compound, for example, $Co_2(CO)_8$, in the tertiary nitrogen base cocatalyst and alcohol at room temperature under a nitrogen blanket, and pressurizing with CO.

EXAMPLE 1

In each of a series of runs, 15 g of dicobalt octacarbonyl was dissolved in 60 g of methanol and 40 g of pyridine at room temperature under nitrogen. The resulting solution, along with 23 g of butadiene (0.43 moles), was pressurized to 5000 psig with carbon monoxide and held at 135° C. with stirring for 3 hrs. The yields of methyl pentenoate were 87±1% for all runs at 99% butadiene conversion. The unit was then cooled to 40° C., vented to 1000 psig, injected with 14 g of the inert diluent specified in Table 1 containing 6 g of acetic acid (0.1 mole), and then heated to 175° C. with continued stirring. The unit was then pressurized to 3000 psig with CO and held there for 2 hrs. The methyl pentenoate conversion varied between 52–87% in the various tests, with yields as shown in Table I.

TABLE I

| Inert Diluent | Percent Yield | | | | |
|---|---|---|---|---|---|
| | Dimethyladipate | Dimethyl-methy gluterate | Dimethylethyl succinate | Dimethyl-propyl-malonate | Methyl valerate |
| Dimethyl Suberate | 71 | 12 | 3.5 | 0.4 | 13 |
| Cyclohexane | 71 | 13 | 4.0 | 1.0 | 13 |
| Methyl 3-pentenoate | 70 | 13 | 4.1 | 0.8 | 13 |
| Methyl valerate | 68 | 12 | 3.0 | 0.4 | 17 |
| Methyl 3-pentenoate | 71 | 12 | 3.7 | 0.4 | 13 |

CONTROL FOR EXAMPLE 1—No acid added

A 22.2 g sample of dicobalt octacarbonyl was dissolved in 60 g of methanol and 70 g of pyridine under an inert atmosphere at room temperature. The resulting solution, along with 23.1 g of butadiene (0.43 moles) was pressurized to 2600 psig with carbon monoxide and 177 atx heated to 135° C. with stirring at 2000 rpm.

After 2 hrs at 135° C., an 82.9% yield of methyl pentenoates was obtained at a 98% conversion of butadiene.

The product was cooled to room temperature and vented to atmospheric pressure to purge unreacted butadiene. After repressuring to 2600 psig with CO, the solution was heated at 175° for 4 hrs. A 52% yield of dimethyladipate was observed at 58% methyl pentenoate conversion. Note that this yield is significantly lower than the 68 to 71% yields shown in Table I.

EXAMPLE 2

In this example only the second step of the process of the invention is illustrated. The starting material for this example was prepared by mixing ingredients in the approximate proportions that they would exist if the methyl 3-pentenoate were prepared under typical conditions from butadiene, carbon monoxide, methanol, cobalt octacarbonyl and pyridine. The example demonstrates that by the addition of an alkanoic acid, i.e., acetic acid, the catalyst is only partially deactivated.

Under a nitrogen atmosphere, 22.2 g of dicobalt octacarbonyl was dissolved in 60 g of methanol and 30 g of pyridine. The resultant solution was mixed in an autoclave with 15.5 g of acetic acid (0.26 moles), 20 g of dimethylsuberate, and 50 g of methyl 3-pentenoate (0.44 moles). The unit was pressurized to 1000 psig with CO, heated to 175° C., pressurized with stirring at 2000 rpm to 5000 psig with CO and then held at this condition for 45 mins.

The yield to dimethyladipate was 65% at 99% methyl pentenoate conversion. Analysis of the catalyst by differential pulse polarography shows only 17% deactivation.

EXAMPLE 3

A 7.4 g sample of dicobalt octacarbonyl was dissolved in 60 g of methanol and 20 g of pyridine at room temperature under a nitrogen atmosphere. The resulting solution was mixed with 50 g of methyl 3-pentenoate and 6 g of acetic acid, pressurized to 2500 psig with carbon monoxide and held at 175° C. for 2 hours with stirring. The yield of dimethyladipate was 73% at 81% pentenoate conversion. Based upon intermediate samples, the reaction halflife for pentenoate consumption was 23.2 minutes. Only 3% of the cobalt catalyst had been deactivated over the 2 hour run, resulting in the loss of 0.5% of the initial pyridine.

Control for EXAMPLE 3

The previous experiment was repeated exactly except that no acetic acid was added. The yield of dimethyladipate was 72% at 42% pentenoate conversion. The reaction halflife for pentenoate consumption was 53.3 minutes. During the 2 hour run, 34% of the cobalt catalyst was deactivated, resulting in the conversion of 6% of the pyridine to N-methylpyridinium ion.

I claim:

1. A process for the preparation of dialkyl adipate which comprises adding to a mixture containing alkyl 3-pentenoate, cobalt catalyst, a tertiary nitrogen base cocatalyst, a lower alkyl alcohol, and carbon monoxide, an amount of an alkanoic acid having a pKa of greater than 3 in an amount sufficient to keep the cobalt catalyst active and reacting the resulting mixture to form alkyl adipate by the carboalkyxylation of alkyl 3-pentenoate.

2. A process for the carboxyalkoxylation of butadiene to form dialkyl adipate by the successive addition of carbon monoxide and lower alkyl alcohol which comprises (a) reacting a mixture comprising butadiene, carbon monoxide and lower alkyl alcohol with a cobalt catalyst and a tertiary nitrogen base cocatalyst, at a cobalt concentration of at least about 0.5 moles per liter of the liquid reaction mixture, and a tertiary nitrogen base cocatalyst concentration of between about 2.3 and 2.9 moles per liter of the liquid reaction mixture to form a liquid mixture containing alkyl 3-pentenoate, (b) adding to the mixture formed in step (a) alkanoic acid having a pKa greater than 3 in an amount sufficient to keep the cobalt catalyst active, but less than about 1 mole per liter of liquid mixture formed in step (a), (c) reacting the mixture formed in step (b) to form dialkyl adipate.

3. The process of claim 2 in which the cobalt catalyst is cobalt carbonyl, the tertiary nitrogen base cocatalyst is pyridine, and the alkanoic acid is 2-8 carbon mono or diacid or a mixture of such acids, and the lower alkyl alcohol is methanol.

4. The process of claim 2 in which the mixture reacted in step (b) contains an alkanoic acid having a pKa of between about 4 and 5.

5. The process of claim 4 in which the alkanoic acid is selected from the group consisting of acetic, adipic, valeric, methylglutaric, and ethyl succinic.

6. The process of claim 2 in which step (a) is carried out at a pressure of at least 100 atmospheres, and at a temperature in the range of about 80° to 150° C.

7. The process of claim 6 in which an inert diluent is added to the mixture formed after the completion of the reaction of step (a), the amount of inert diluent being sufficient to reduce the concentration of the components of the mixture by 5 to 15%.

8. The process of claim 6 in which step (b) is carried out at a pressure of at least 100 atmospheres and at a temperature in the range of about 140° to 200° C.

9. The process of claim 1 in which the amount of alkanoic acid is between about 0.05 and about one mole per liter of the mixture containing alkyl 3-pentenoate.

10. The process of claim 9 in which the amount of alkanoic acid added in between about 0.05 and 0.5 mole per liter of the mixture containing alkyl 3-pentenoate.

11. The process of claim 1 in which the tertiary nitrogen base cocatalyst is pyridine.

* * * * *